(12) United States Patent
Crutchfield et al.

(10) Patent No.: US 10,737,090 B2
(45) Date of Patent: Aug. 11, 2020

(54) EXTERNAL DEFIBRILLATION ELECTRODE CONDUCTIVE ELECTROLYTE DISPERSAL PAD

(71) Applicant: Medtronic, Inc., Minneapolis, MN (US)

(72) Inventors: Randolph E. Crutchfield, Scottsdale, AZ (US); Gerard A. Bast, Chandler, AZ (US); David A. Cano, Phoenix, AZ (US); Lisa Anne Harness Mesias, Chandler, AZ (US); Clark B. Norgaard, Phoenix, AZ (US); Mark E. Porter, Phoenix, AZ (US); Jerome Sims, II, Phoenix, AZ (US); Philip Timson, Phoenix, AZ (US)

(73) Assignee: Medtronic, Inc., Minneapolis, MN (US)

( * ) Notice: Subject to any disclaimer, the term of this patent is extended or adjusted under 35 U.S.C. 154(b) by 272 days.

(21) Appl. No.: 15/646,901

(22) Filed: Jul. 11, 2017

(65) Prior Publication Data

US 2019/0015657 A1 Jan. 17, 2019

(51) Int. Cl.
*A61N 1/04* (2006.01)
*A61N 1/39* (2006.01)
*A61N 1/08* (2006.01)

(52) U.S. Cl.
CPC .......... *A61N 1/046* (2013.01); *A61N 1/0484* (2013.01); *A61N 1/0496* (2013.01);
(Continued)

(58) Field of Classification Search
CPC .... A61N 1/046; A61N 1/0412; A61N 1/0484; A61N 1/042; A61N 1/0428;
(Continued)

(56) References Cited

U.S. PATENT DOCUMENTS 5,078,134 A  1/1992 Heilman et al.
5,797,898 A  8/1998 Santini, Jr. et al.
(Continued)

FOREIGN PATENT DOCUMENTS

WO  2016077236  5/2016

OTHER PUBLICATIONS

International Search Report and Written Opinion of International Application No. PCT/US2018/041658, dated Sep. 26, 2018, 13 pp.
(Continued)

*Primary Examiner* — Tammie K Marlen

(57) ABSTRACT

An external defibrillator system may include processing circuitry; signal generation circuitry communicatively coupled to the processing circuitry; and a plurality of electrodes, each including an electrode body electrically coupled to the signal generation circuitry and configured to deliver an electrical pulse therapy to a patient; and an electrolyte dispersal pad that includes a substrate defining a plurality of wells, each defining an opening; an electrolyte material, e.g., fluid, disposed within at least a portion of the plurality of wells; and a conductive material disposed over at least a portion of the openings and configured to retain the electrolyte material within the plurality of wells, where the processing circuitry is configured control the signal generation circuitry to pass a current pulse through a portion of the conductive material to fuse the portion of the conductive material to release the electrolyte material from at least one of the wells.

44 Claims, 6 Drawing Sheets

(52) U.S. Cl.
CPC ......... *A61N 1/3912* (2013.01); *A61N 1/3925* (2013.01); *A61N 1/3987* (2013.01); *A61N 1/08* (2013.01); *A61N 1/3904* (2017.08)

(58) Field of Classification Search
CPC .. A61N 1/0436; A61N 1/0448; A61N 1/0444; A61N 1/0496
See application file for complete search history.

(56) References Cited

U.S. PATENT DOCUMENTS

| | | |
|---|---|---|
| 5,944,669 A | 8/1999 | Kaib |
| 6,065,154 A | 5/2000 | Hulings et al. |
| 6,097,982 A | 8/2000 | Glegyak et al. |
| 6,123,861 A | 9/2000 | Santini, Jr. et al. |
| 6,169,387 B1 | 1/2001 | Kaib |
| 6,253,099 B1 | 6/2001 | Oskin et al. |
| 6,280,461 B1 | 8/2001 | Glegyak et al. |
| 6,681,003 B2 | 1/2004 | Linder et al. |
| 6,808,522 B2 | 10/2004 | Richards et al. |
| 7,052,488 B2 | 5/2006 | Uhland |
| 7,070,592 B2 | 7/2006 | Santini, Jr. et al. |
| 7,269,462 B2 | 9/2007 | White et al. |
| 7,455,667 B2 | 11/2008 | Uhland et al. |
| 7,537,590 B2 | 5/2009 | Santini, Jr. et al. |
| 7,892,221 B2 | 2/2011 | Santini, Jr. et al. |
| 7,901,397 B2 | 3/2011 | Santini, Jr. et al. |
| 7,910,151 B2 | 3/2011 | Uhland et al. |
| 7,918,842 B2 | 4/2011 | Santini, Jr. et al. |
| 8,016,817 B2 | 9/2011 | Santini, Jr. et al. |
| 8,211,092 B2 | 7/2012 | Uhland et al. |
| 8,406,842 B2 | 3/2013 | Kaib et al. |
| 8,904,214 B2 | 12/2014 | Volpe et al. |
| 9,037,271 B2 | 5/2015 | Kaib et al. |
| 9,132,267 B2 | 9/2015 | Kaib |
| 9,272,131 B2 | 3/2016 | Kaib |
| 9,345,898 B2 | 5/2016 | Piha et al. |
| 9,393,437 B2 | 7/2016 | Meeker |
| 2011/0288604 A1 | 11/2011 | Kaib |
| 2014/0207201 A1* | 7/2014 | Piha ............... A61N 1/3918 607/4 |
| 2014/0213875 A1 | 7/2014 | Freeman et al. |
| 2014/0249613 A1 | 9/2014 | Kaib |
| 2015/0283391 A1 | 10/2015 | Meeker |
| 2016/0235995 A1 | 8/2016 | Piha et al. |
| 2016/0271384 A1 | 9/2016 | Kaib |
| 2016/0375262 A1 | 12/2016 | Meeker |

OTHER PUBLICATIONS

International Preliminary Report on Patentability from International Application No. PCT/US2018/041658, dated Jan. 23, 2020, 8 pp.

* cited by examiner

EXTERNAL DEFIBRILLATION ELECTRODE CONDUCTIVE ELECTROLYTE DISPERSAL PAD

TECHNICAL FIELD

This disclosure relates to systems and methods for dispersal of conductive electrolyte materials for external defibrillation electrodes.

BACKGROUND

Malignant tachyarrhythmia, for example, ventricular fibrillation, is an uncoordinated contraction of the cardiac muscle of the ventricles in the heart, and is the most commonly identified arrhythmia in cardiac arrest patients. If this arrhythmia continues for more than a few seconds, it may result in cardiogenic shock and cessation of effective blood circulation. Consequently, sudden cardiac death (SCD) may result in a matter of minutes.

During a malignant tachyarrhythmia event, the use of an Automatic External Defibrillator (AED) system has been shown to be beneficial at preventing SCD. An AED uses strategically placed electrodes to provide one or more defibrillation electric pulses to the heart of a subject. Because of the large energies of the defibrillation electric pulse, the electrodes may benefit from reduced impedance and increased surface area contact at the electrode/skin interface to reduce potential damage of the body tissue of the subject and to facilitate delivery of the electrical pulse therapy. Low impedance interface fluids may be used to reduce impedance and increase surface area at the electrode/skin interface. For a wearable AED (WAED), it may be desirable for the low impedance interface fluid to be dispensed at the electrode/skin interface automatically. Such systems may involve bulky or uncomfortable low impedance interface fluid dispensing units near the electrodes and/or pumps to deliver the low impedance interface fluid to the electrode/skin interface before delivering one or more defibrillation electric pulses to the heart of a subject.

SUMMARY

In some examples, the disclosure describes an external defibrillator system that includes processing circuitry; signal generation circuitry communicatively coupled to the processing circuitry; and a plurality of electrodes, each electrode including an electrode body electrically coupled to the signal generation circuitry and configured to deliver an electrical pulse therapy to a patient; and an electrolyte dispersal pad over the electrode body, wherein the electrolyte dispersal pad includes a substrate defining a plurality of wells, each respective well defining an opening; an electrolyte material disposed within the plurality of wells; and a conductive material disposed over at least a portion of the plurality of openings and configured to retain the electrolyte material within the plurality of wells, where the processing circuitry is configured control the signal generation circuitry to pass a current pulse through a portion of the conductive material to fuse the portion of the conductive material to release the electrolyte material from at least one of the wells.

In some examples, the disclosure describes an external defibrillator electrode electrolyte dispersal pad that includes a substrate defining a plurality of wells, each respective well defining an opening; an electrolyte material disposed within the plurality of wells; and a conductive material disposed over at least a portion of the plurality of openings and configured to retain the electrolyte material within the plurality of wells, where the conductive material is configured to receive a current pulse through a portion of the conductive material to fuse the portion of the conductive material to release the electrolyte material from at least one of the wells.

In some examples, the disclosure describes a method that includes sensing, by an sensing circuitry communicatively coupled to a plurality of electrodes, a cardiac event in a heart of a patient, where each respective electrode includes an electrode body electrically coupled to a signal generation circuitry and configured to deliver an electrical pulse therapy to the patient; and an electrolyte dispersal pad over the electrode body, wherein the electrolyte dispersal pad includes a substrate defining a plurality of wells, each respective well defining an opening; an electrolyte material disposed within the plurality of wells; and a conductive material disposed over at least a portion of the plurality of openings and configured to retain the electrolyte material within the plurality of wells; determining, by a processing circuitry communicatively coupled to the sensing circuitry, in response to the sensed cardiac event, to deliver an electrical pulse therapy to the patient; and releasing the electrolyte solution from at least one of the wells by controlling, by the processing circuitry, the signal generation circuitry to pass a current pulse through a portion of the conductive material to fuse the portion of the conductive material to release the electrolyte material from at least one of the wells.

In some examples, a wearable external defibrillator system comprises processing circuitry; signal generation circuitry communicatively coupled to the processing circuitry; and a plurality of electrodes. Each respective electrode comprises an electrode body electrically coupled to the signal generation circuitry and configured to deliver an electrical pulse therapy to a patient; and an electrolyte dispersal pad over the electrode body wherein the electrolyte dispersal pad is conformal to a contour of a surface of a skin of the patient. The electrolyte dispersal pad comprises a substrate defining a plurality of wells, each respective well defining an opening; an electrolyte material disposed within the plurality of wells, wherein the electrolyte material is configured to reduce the impedance between the skin of the patient and the electrode body during an electrical pulse therapy and increase the surface area on the skin of the patient through which an electrical pulse passes during an electrical pulse therapy; and a conductive material disposed over at least a portion of the plurality of openings and configured to retain the electrolyte material within the plurality of wells, wherein the processing circuitry is configured control the signal generation circuitry to pass a current pulse through a portion of the conductive material to fuse the portion of the conductive material to release the electrolyte material from at least one of the wells prior to controlling the signal generation circuitry to deliver an electrical pulse therapy to the patient.

The details of one or more aspects of the disclosure are set forth in the accompanying drawings and the description below. Other features, objects, and advantages of the disclosure will be apparent from the description and drawings, and from the claims.

DETAILED DESCRIPTION

Figure 1:
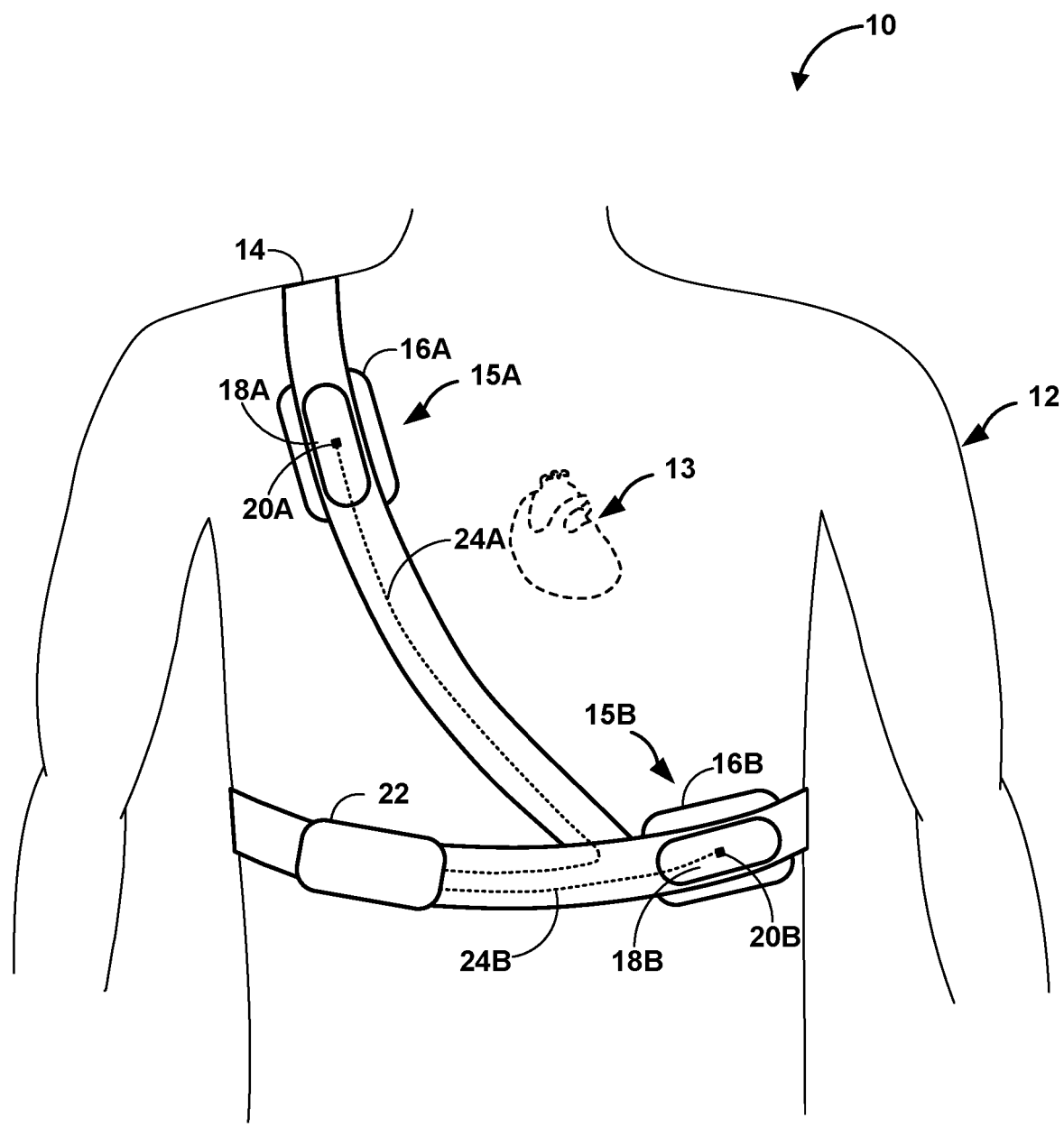
FIG. 1 is a conceptual diagram illustrating an example system that may be used to provide therapy to a heart of a patient.

This disclosure describes systems and techniques for dispersal of a conductive electrolyte material, e.g., in the context of a wearable external defibrillation system. Example systems may include a signal generation circuitry, which can provide an electrical pulse or shock therapy to a user via electrodes. The signal generation circuitry may further provide one or more current pulses to a conductive material covering electrolyte material containing wells of an electrolyte dispersal pad on or incorporated in the body of the electrode. The one or more current pulses may fuse the conductive material, thereby releasing the electrolyte material. Example techniques may include determining, in response to a sensed cardiac event, to deliver an electrical pulse therapy to a wearer and releasing, in response to the determination and prior to the electrical pulse therapy, an electrolyte material, e.g., fluid or powder, from wells by fusing, with a current pulse, at least a portion of a conductive material covering the wells.

In some examples, a Wearable Automatic (or Automated) External Defibrillator (WAED) may use strategically placed electrodes to provide an electrical pulse therapy to the heart of a wearer. For example, two or more electrodes of the WAED may be held against the skin of the wearer by a garment. The electrodes may be positioned to form a vector that may pass the electrical pulse therapy through at least a portion of the heart tissue of the wearer. In some examples, the electrical pulse therapy may include a high-energy electrical pulse. The high-energy electrical pulse may include sufficient energy to disrupt or alter a cardiac tachyarrhythmia in the heart of the wearer. For example, the electrical pulse may depolarize the heart muscle. Depolarization of the heart muscle may stop the beating of the heart. Stopping the heart may eliminate a tachyarrhythmia (e.g., a ventricular tachycardia, a ventricular fibrillation, or the like). After being stopped, the sinoatrial (SA) node may naturally reset to restore a normal sinus rhythm (NSR). In some examples, an electrical pulse therapy may be used to pace the heartbeat. For example, post-shock pacing may aid in restoring NSR.

In some examples, WAED systems may benefit from improved electrical contact between the electrodes and the skin of the wearer. A degree of electrical contact between the electrodes and the skin of the wearer may be determined, at least in part, by an impedance between the electrode and the skin of the wearer, and/or a surface area of the electrical contact of each electrode on the skin of the wearer. The impedance at the electrode/skin interface may be increased by, for example, clothing between the electrode body surface and the skin of the wearer, an air gap between at least a portion of the electrode body surface and the skin of the wearer, dry skin of the wearer, or the like. In some examples, insufficient electrical contact with the skin of the wearer may result in damage to the tissue of the wearer from the high-energy electric pulse, reduce the effectiveness of the electrical pulse therapy, or both. In some examples, electrical contact may be improved by reducing the impedance between the electrode and the skin of the wearer, increasing the surface area of the electrical contact on the skin of the wearer, or both.

In some examples, electrical contact between the electrodes and the skin of the wearer may be improved by an electrolyte material, e.g., fluid or powder, between the electrodes and the skin of the wearer. An electrolyte material between the electrodes and the skin of the wearer may reduce the impedance between the electrodes and the skin of the wearer by, for example, wetting the clothing, other material between the electrode and skin, and/or skin of the wearer in an electrolyte fluid, allowing the area of electrical contact to conform to a curvature of the skin of the wearer to reduce gaps between the electrode body surface and the skin of the wear, or the like. The electrolyte material between the electrodes and the skin of the wearer also may increase the surface area of the electrode body in electrical contact with the skin of the wear by, for example, allowing the area of electrical contact to conform to a curvature of the skin of the wearer to reduce gaps between the electrode body surface and the skin of the wearer, making an area beyond the electrode body electrically conductive via the electrolyte fluid to increase the total surface area of electrical connection with the skin, or the like.

In some examples, an electrolyte dispersal pad on the electrode body may release an electrolyte material into the electrode/skin interface. For example, WAED system may include an electrolyte dispersal pad on or within the electrode body, e.g., each of two or more electrode bodies. The electrolyte dispersal pad may include substrate having wells containing an electrolyte material. The wells may be covered by a conductive material.

The conductive material may be configured to receive a current pulse. The current pulse may fuse at least a portion of the conductive material. Fusing a portion of the conductive material may release at least a portion of the electrolyte material. In some examples, the WAED system including electrolyte dispersal pads configured as described herein may include electrodes that may be thinner or less bulky compared to electrodes with other proposed electrolyte dispersal mechanisms. In some examples, the WAED system including electrolyte dispersal pads configured as described herein may deliver the electrolyte material, e.g., fluid or powder, to the electrode/skin interface more quickly compared to electrodes with other proposed electrolyte dispersal mechanisms. In this way, the disclosure describes WAED systems and electrical pulse therapy delivery techniques that may reduce the impedance at, and increase the surface area of, the electrode/skin interface.

FIG. 1 is a conceptual diagram illustrating an example WAED system 10 that may be used to provide electrical pulse therapy to a heart 13 of a wearer 12. WAED system 10 may include a wearable garment 14 holding electrodes 15A and 15B (collectively, "electrodes 15") that may be connected to WAED controller 22 via electrode leads 24A and 24B (collectively, "electrode leads 24").

In some examples, WAED system 10 may be worn by wearer 12. For example, garment 14 may be configured to hold WAED controller 22 and/or electrodes 15 against the body of wearer 12. In some examples, garment 14 may include a textile harness, shirt, strap, vest, or the like. In some examples, garment 14 may include an adhesive patch or strip. In some examples, garment 14 may include a combination of an adhesive and a textile. For example, a textile shirt, strap, vest, or the like may include adhesive in one or more locations to aid in holding AED controller 22 and/or electrodes 15 against the body of wearer 12. In some examples, WAED controller 22 may be adjustably positioned on garment 14 such that wearer 12 may interact with WAED controller 22. For example, wearer 12 may be able to view, hear, tactilely feel, or manipulate, or any combination thereof, WAED controller 22. In other examples, WAED controller 22 may be adjustably positioned on garment 14 such that another user, e.g., a first-responder or another third-party, may view, hear, manipulate, or any combination thereof, WAED controller 22.

In some examples, electrodes 15 may be adjustably positioned on garment 14 such that an electrical pulse therapy vector between electrodes 15 may substantially cross at least a portion of heart 13. For example, the location and orientation of electrodes 15 relative to each other and to heart 13 may be adjustable. In some examples, the location and orientation of electrodes 15 may be adjusted to provide a desirable electrical pulse therapy vector. The electrical pulse therapy vector may, in one example, be viewed as a line that extends from a point on electrode 15A, e.g., the center of electrode 15A, to a point on electrode 15B, e.g., the center of electrode 15B. In some examples, the electrical pulse therapy vector may be substantially across the ventricle(s) of heart 13. In some examples, the electrical pulse therapy vector may be substantially across the right ventricle of heart 13. Although illustrated in FIG. 1 as including two electrodes 15, the illustrated positions and number of electrodes 15 is merely an example. Any number of electrodes 15 may be positioned in a variety of positions on wearer 12 to provide a variety of vector options, including posterior and anterior options.

Electrodes 15 may include electrolyte dispersal pads 16A and 16B (collectively, "electrolyte dispersal pads 16") between the skin of wearer 12 and electrode bodies 18A and 18B (collectively, "electrode bodies 18") electrically coupled to electrode leads 24 via electrode connections 20A and 20B (collectively, "electrode connections 20"). Electrodes 15 may be configured to pass an electric pulse therapy through heart 13 of wearer 12. For example, electrode bodies 18 may include a flat ribbon electrode, paddle electrode, braided or woven electrode, mesh electrode, segmented electrode, directional electrode, patch electrode, or the like. Electrode bodies 18 may include any suitable electrically conductive material. For example, electrode bodies 18 may include biocompatible (e.g., pharmacologically inert, nontoxic, and the like) and sterilizable electrically conductive materials, such as, for example, titanium.

In some examples, electrodes 15 may be configured to sense one or more signals from wearer 12. For example, electrodes 15 may be configured to sense electrical signals produced by heart 13, respiration rate of wearer 12, tissue perfusion of wearer 13, or the like. In some examples, electrodes 15 may be configured to sense an impedance at the electrode/skin interface. For example, the electrode/skin interface may include one or more textile layers between a surface of electrode 15 and the skin of wearer 12 that may affect impedance at the electrode/skin interface. As another example, the electrode/skin interface may include one or more fluids, e.g., sweat of wearer 12 or an electrolyte fluid released by electrode 15, that may affect impedance at the electrode/skin interface.

Electrode bodies 18 may include a first major surface adjacent at least a portion of the skin of wearer 12. In some examples, the resistivity of electrode bodies 18 may depend, at least in part, on the surface area of the first major surface.

For example, a larger surface area may have a lesser resistivity compared to a smaller surface area of electrode bodies 18. The surface area of the first major surface of electrode bodies 18 may be sized, for example, to pass a desired electric current into electrolyte dispersal pads 16. For example, the surface area of electrode bodies 18 may be between about 5 square centimeters ($cm^2$) and about 500 $cm^2$, or between about 50 square centimeters ($cm^2$) and about 135 $cm^2$. In this way, electrode bodies 18 may be configured to pass a desired amount of electric current through electrolyte dispersal pads 16.

Electrolyte dispersal pads 16 may be disposed between electrode bodies 18 and the skin of the wearer. In some examples, electrolyte dispersal pads 16 may be electrically coupled to electrode bodies 18. For example, electrolyte dispersal pads 16 may include a conductive material in electrical contact with at least a portion of electrode bodies 18. In some examples, electrolyte dispersal pads 16 may include a first major surface defining the electrode/skin interface. In some examples, the resistivity of electrolyte dispersal pads 16 may depend, at least in part, on the surface area of the first major surface of the electrolyte dispersal pads 16. For example, a larger surface area may have a lesser resistivity compared to a smaller surface area. The surface area of the first major surface of electrolyte dispersal pads 16 may be sized, for example, to pass a desired electric current through heart 13 of wearer 12 via the electrode/skin interface. For example, the surface area o of the first major surface of electrolyte dispersal pads 16 may be between about 5 square centimeters ($cm^2$) and about 500 $cm^2$, or between about 50 square centimeters ($cm^2$) and about 135 $cm^2$. In this way, electrolyte dispersal pads 16 may be configured to conduct an electric current from electrode bodies 18 through the electrode/skin interface and through heart 13 of wearer 12.

Electrode leads 24 may be formed from a non-conductive material, including, for example, silicone, polyurethane, other appropriate material, or mixtures thereof, and shaped to form one or more lumens within which one or more electrical conductors extend. However, the techniques are not limited to such constructions. The one or more electrical conductors may engage with respective electrodes 15. For example, one or more electrical conductors may engage with respective electrode connections 20, electrode bodies 18, or electrode dispersal pads 16. In one example, each of a plurality of electrical conductors within a respective electrode leads 24 may be electrically coupled to a respective portion of electrode dispersal pads 16.

In some examples, electrode leads 24 may be physically coupled to electrode bodies 18 by electrode connections 20. Electrode connections 20 may include any suitable electrically conductive material. For example, electrode connections 20 may include conductive metals (e.g., titanium, copper, silver, gold, aluminum, or the like) or other conductive materials (e.g., carbon, silicon, or the like). In some examples, electrode connections 20 may include detachable connections, e.g., binding post, plug and socket, blade connectors, ring and spade terminals, or other keyed or unkeyed electrical connectors. In other examples, electrode connections 20 may include permanent or semi-permanent connections, e.g., soldered connections. In some examples, the respective conductors of electrode leads 24 may electrically couple to circuitry of WAED controller 22 via one or more terminals. For example, the respective conductors may electrically couple one or more of sensing circuitry, signal generation circuitry, or switching circuitry of WAED controller 22.

Figure 2:
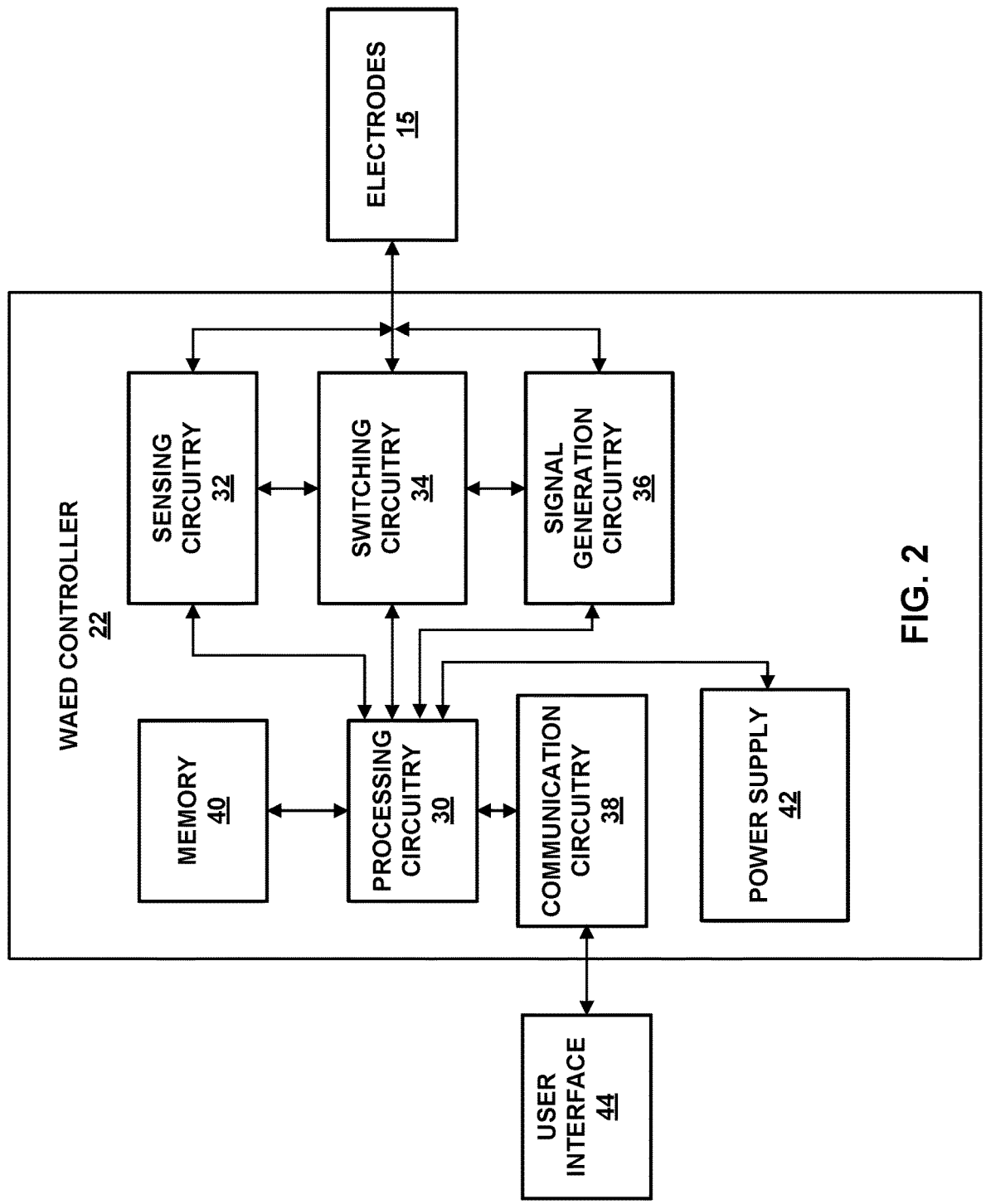
FIG. 2 is a functional block diagram illustrating an example configuration of the system shown in FIG. 1.

WAED controller 22 may be configure to deliver an electric pulse therapy in response to a sensed cardiac event. For example, FIG. 2 is a functional block diagram illustrating an example configuration of the WAED controller 22 shown in FIG. 1. WAED controller 22 includes processing circuitry 30, sensing circuitry 32, switching circuitry 34, signal generation circuitry 36, communication circuitry 38, and memory 40. The electronic components of WAED controller 22 may receive power from a power source 42. For example, power source 42 may be a rechargeable or non-rechargeable battery. In some examples, power source 42 may be configured to produce a desired voltage and amperage of a desired duration and waveshape to deliver an electric pulse therapy to heart 13. In other examples, WAED controller 22 may include more or fewer electronic components. The described circuitry units may be implemented together on a common hardware component or separately as discrete but interoperable hardware, firmware or software components. Depiction of different features as circuitry units is intended to highlight different functional aspects and does not necessarily imply that such circuitry units must be realized by separate hardware, firmware or software components. Rather, functionality associated with one or more circuitry units may be performed by separate hardware, firmware or software components, or integrated within common or separate hardware, firmware or software components.

Sensing circuitry 32 is electrically coupled to some or all of electrodes 15 via the conductors of electrode leads 24 and one or more electrical and/or physical connectors and/or feedthroughs on a housing of WAED controller 22. Sensing circuitry 32 may be configured to obtain signals sensed via one or more combinations of electrodes 15 or other sensing devices, and process the obtained signals. In some examples, WAED controller may include sensing circuitry configured to sense a cardiac event, such as a cardiac arrhythmia. For example, WAED controller 22 may receive from electrodes 15 or another other sensing device one or more electrical signals indicative of electrical signals produced by heart 13, respiration rate of wearer 12, tissue perfusion of wearer 13, or the like.

The components of sensing circuitry 32 may be analog components, digital components, or a combination thereof. Sensing circuitry 32 may, for example, include one or more sense amplifiers, filters, rectifiers, threshold detectors, analog-to-digital converters (ADCs) or the like. Sensing circuitry 32 may convert the sensed signals to digital form and provide the digital signals to processing circuitry 30 for processing or analysis. For example, sensing circuitry 32 may amplify signals from electrodes 15 and convert the amplified signals to multi-bit digital signals by an ADC. Sensing circuitry 32 may also compare processed signals to a threshold to detect the existence of atrial or ventricular depolarizations (e.g., P- or R-waves) and indicate the existence of the atrial depolarization (e.g., P-waves) or ventricular depolarizations (e.g., R-waves) to processing circuitry 30. In some examples, processing circuitry 30 may control sensing circuitry 32 to measure other parameters, such as body or electrode/wearer interface impedance measurements of wearer 12 via electrodes 15.

Processing circuitry 30 may process the signals from sensing circuitry 32 to monitor electrical activity of heart 13 of wearer 12. Processing circuitry 30 may store signals obtained by sensing circuitry 32 as well as any generated EKG waveforms, marker channel data or other data derived based on the sensed signals in memory 40. Processing circuitry 30 also may analyze the EKG waveforms and/or marker channel data to detect cardiac events (e.g., tachycardia). In response to detecting the cardiac event, processing circuitry 30 may control signal generation circuitry 36 to generate and deliver the desired electric pulse therapy according to one or more therapy programs, which may be stored in memory 40, to treat the cardiac event. The therapy may include, but is not limited to, defibrillation or cardioversion shock(s), anti-tachyarrhythmia pacing (ATP), post-shock pacing, bradycardia pacing, or the like.

Signal generation circuitry 36 is configured to generate and deliver electric pulse therapy to heart 13. Signal generation circuitry 36 may include one or more pulse generators, capacitors, and/or other components capable of generating and/or storing energy to deliver as defibrillation therapy, cardioversion therapy, cardiac resynchronization therapy, other electric pulse therapy or a combination of therapies. In some instances, signal generation circuitry 36 may include a first set of components configured to provide pacing therapy and a second set of components configured to provide defibrillation therapy. In other instances, the same set of components may be configurable to provide both pacing and defibrillation therapy. In still other instances, some of the defibrillation and pacing therapy components may be shared components while others are used solely for defibrillation or pacing. In these ways, signal generation circuitry 36 may be configured to use energy from power source 42 to deliver an electrical pulse therapy.

Signal generation circuitry 36 delivers the generated therapy to heart 13 via one or more combinations of electrodes 15. Processing circuitry 30 controls signal generation circuitry 36 to generate electrical stimulation therapy with the amplitudes, pulse widths, timing, frequencies, or electrode combinations specified by the selected therapy program.

In the case of pacing therapy, e.g., post-shock pacing and/or bradycardia pacing provided via electrodes 15, processing circuitry 30 controls signal generation circuitry 36 to generate and deliver pacing pulses with any of a number of amplitudes and pulse widths to capture heart 13. The pacing thresholds of heart 13 may depend upon a number of factors, including location, type, size, orientation, and/or spacing of electrodes 15, physical abnormalities of heart 13 (e.g., pericardial adhesions or myocardial infarctions), or other factor(s).

In some examples, signal generation circuitry 36 may generate and deliver pacing pulses having any suitable amplitudes and any suitable pulse widths. For example, signal generation circuitry 36 may generate and deliver pacing pluses having amplitudes of between about 10 volts and about 100 volts and pulse widths between about 2 milliseconds and about 10 milliseconds.

In some examples, signal generation circuitry 36 may be configured to generate and deliver pacing pulses having pulse widths or durations of greater than two (2) milliseconds. In other examples, signal generation circuitry 36 may be configured to generate and deliver pacing pulses having pulse widths or durations of between greater than two (2) milliseconds and less than or equal to three (3) milliseconds. In another example, signal generation circuitry 36 may be configured to generate and deliver pacing pulses having pulse widths or durations of greater than or equal to three (3) milliseconds. In another example, signal generation circuitry 36 may be configured to generate and deliver pacing pulses having pulse widths or durations of greater than or equal to five (5) milliseconds. In another example, signal generation circuitry 36 may be configured to generate and deliver pacing pulses having pulse widths or durations of greater than or equal to ten (10) milliseconds. In a further example, signal generation circuitry 36 may be configured to generate and deliver pacing pulses having pulse widths between approximately 3-10 milliseconds. In a further example, signal generation circuitry 36 may be configured to generate and deliver pacing pulses having pulse widths or durations of greater than or equal to fifteen (15) milliseconds. In yet another example, signal generation circuitry 36 may be configured to generate and deliver pacing pulses having pulse widths or durations of greater than or equal to twenty (20) milliseconds.

Depending on the pulse widths, WAED controller 22 may be configured to deliver pacing pulses having pulse amplitudes less than or equal to twenty (20) volts, deliver pacing pulses having amplitudes within a range from ten (10) volts to twenty (20) volts, or deliver pacing pulses having pulse amplitudes less than or equal to ten (10) volts. In other examples, the pacing pulse amplitudes may be greater than 20 volts. Reducing the amplitude of pacing pulses delivered by WAED controller 22 reduces the likelihood of extra-cardiac stimulation.

In the case of defibrillation therapy, e.g., defibrillation or cardioversion shocks provided by electrodes 15, processing circuitry 30 controls signal generation circuitry 36 to generate defibrillation or cardioversion shocks having any of a number of waveform properties, including leading-edge voltage, tilt, delivered energy, pulse phases, and the like. Signal generation circuitry 36 may, for instance, generate monophasic, biphasic or multiphasic waveforms. Additionally, signal generation circuitry 36 may generate defibrillation waveforms having different amounts of energy. For example, signal generation circuitry 36 may generate defibrillation waveforms that deliver a total of between approximately 80-400 Joules (J) of energy. Signal generation circuitry 36 may also generate defibrillation waveforms having different tilts. In the case of a biphasic defibrillation waveform, signal generation circuitry 36 may use a 65/65 tilt, a 50/50 tilt, or other combinations of tilt. The tilts on each phase of the biphasic or multiphasic waveforms may be the same in some instances, e.g., 65/65 tilt. However, in other instances, the tilts on each phase of the biphasic or multiphasic waveforms may be different, e.g., 65 tilt on the first phase and 55 tilt on the second phase. The example delivered energies, leading-edge voltages, phases, tilts, and the like are provided for example purposes only and should not be considered as limiting of the types of waveform properties that may be utilized to provide defibrillation via electrodes 15.

Communication circuitry 38 includes any suitable hardware, firmware, software or any combination thereof for communicating with other devices, such as user interface 44, via a wired or wireless connection. For example, communication circuitry 38 may include appropriate modulation, demodulation, frequency conversion, filtering, and amplifier components for transmission and reception of data with or without the aid of an antenna. In some examples, user interface 44 may be incorporated into and provided by, in whole or in part, WAED controller 22. User interface 44 may any one or more of a display, touch screen, keypad, speaker, microphone, or camera, as examples.

The various circuitry of WAED controller 22, such as processing circuitry 30, may include any one or more processors, controllers, digital signal processors (DSPs), application specific integrated circuits (ASICs), field-programmable gate arrays (FPGAs), or equivalent discrete or integrated circuitry, including analog circuitry, digital circuitry, or logic circuitry. Memory 40 may include computer-readable instructions that, when executed by processing circuitry 30 or other component of WAED controller 22, cause one or more components of WAED controller 22 to perform various functions attributed to those components in this disclosure. Memory 40 may include any volatile, non-volatile, magnetic, optical, or electrical media, such as a random-access memory (RAM), read-only memory (ROM), non-volatile RAM (NVRAM), static non-volatile RAM (SRAM), electrically-erasable programmable ROM (EEPROM), flash memory, or any other non-transitory computer-readable storage media.

Figure 3:
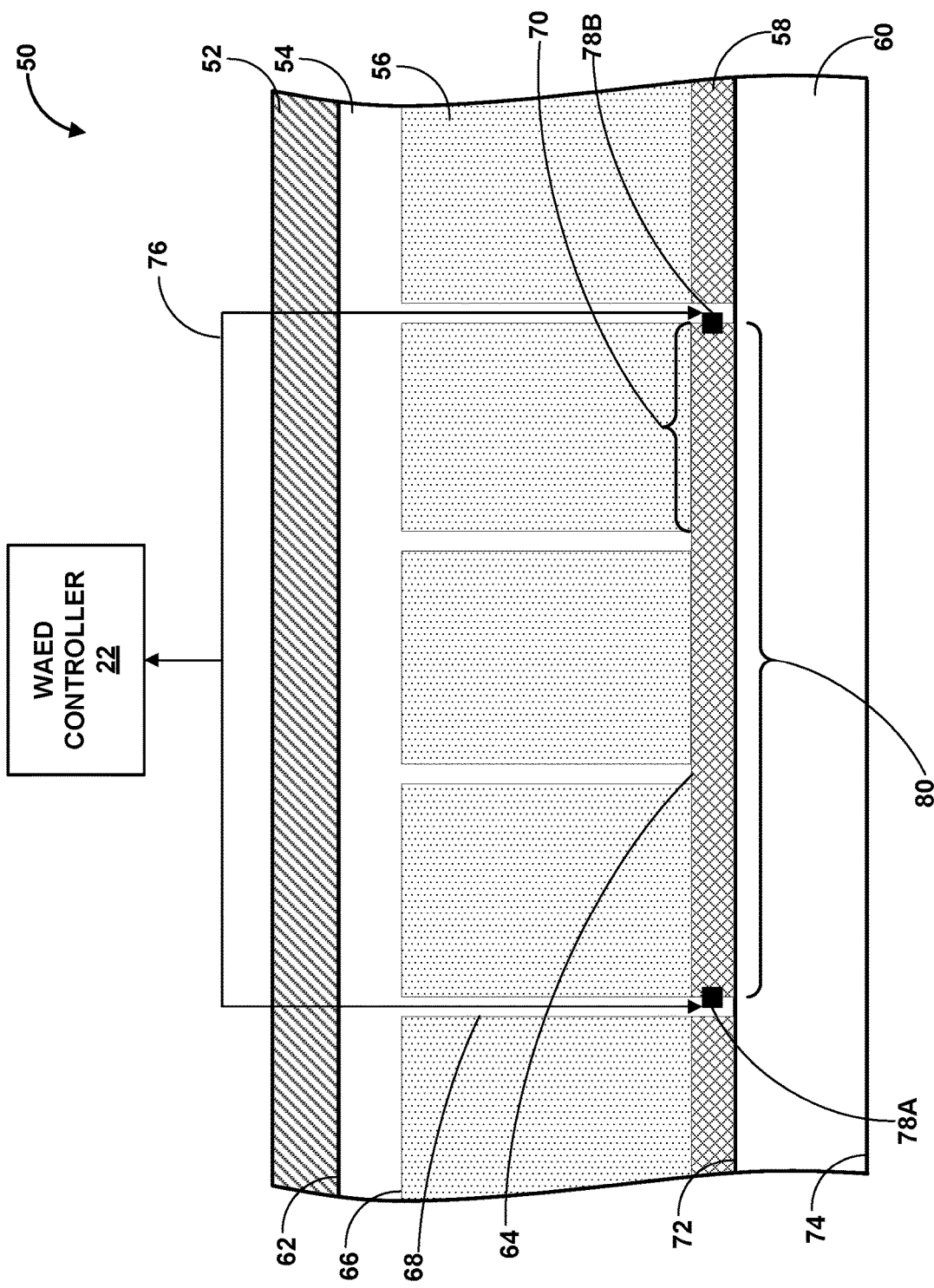
FIG. 3 is a conceptual diagram illustrating an example conductive electrolyte dispersal pad for an electrode of the system shown in FIG. 1.

FIG. 3 is a conceptual diagram illustrating an example electrolyte dispersal pad 50 of a WAED system, for example, WAED system 10. In some examples, electrolyte dispersal pad 50 may include a substrate 54 holding an electrolyte material, e.g., fluid or powder, in a plurality of wells 56 having openings 70 that may be covered in conductive material 58. In some examples, electrolyte dispersal pad 50 may include a protective layer 52 and/or a comfort layer 60.

In some examples, protective layer 52 may include any suitable material for protecting substrate 54, wells 56, or conductive material 58. For example, protective layer may include a non-conductive material (e.g., polyethylene, polypropylene, polyurethane, polyvinylchloride, other polymers, or combinations thereof) and/or a conductive material (e.g., titanium, copper, silver, gold, aluminum, or the like). In some examples, protective layer 52 may be configured to inhibit puncture or breakage of substrate 54 from contact with external objects. In some examples, protective layer may be configured to control a current path from an electrode body (e.g., electrode bodies 18) to substrate 54 or conductive material 58. For example, protective layer 52 may include a non-conductive material and a conductive material is selectively patterned in and extending through at least a portion of the non-conductive material.

In some examples, substrate 54 may include any suitable material in which, or on which, a plurality of wells 56 may be formed. In this way, substrate 54 may be configured to hold an electrolyte material, e.g., fluid or powder. In some examples, substrate 54 may include any suitable electrically conductive or semi-conductive material. In one example, substrate 54 may include silicon. In this way, substrate 54 may be configured to conduct an electric current from an electrode body (e.g., electrode bodies 18) to an electrolyte material and/or conductive material 58. In other examples, substrate 54 may include other materials or combinations of materials. For example, substrate 54 may include conductive and non-conductive materials, such as conductive vias through a non-conductive material. Example, non-conductive materials include glass, sapphire, and polyimide. Example, conductive materials include titanium, copper, aluminum, gold, nickel, platinum, graphite. In this way, substrate 54 may be configured to control a path of current flow through substrate 54.

In some examples, substrate 54 may define one continuous segment. For example, substrate 54 may extend substantially the entire area of electrolyte dispersal pad 50. In other examples, substrate 54 may define multiple segments. For example, multiple segments of substrate 54 may collectively extend substantially the entire area of electrolyte dispersal pad 50. In some examples, multiple segments of substrate 54 may be joined by any suitable material. For example, multiple segments of substrate 54 may be joined by a conductive material (e.g., titanium, copper, silver, gold, aluminum, silicon, or the like) or a nonconductive material (e.g., silicone, rubber, polyethylene, polypropylene, polyurethane, polyvinylchloride, or the like). In some examples, multiple segments of substrate 54 may be adhered to, embedded in, or otherwise affixed to protective layer 52. In some examples, individual segments of multiple segmented parts of substrate 54 may be separately electrically coupled to a respective electrical conductor of an electrode lead (e.g., electrode lead 24 of FIG. 1). In this way, substrate 54 may be configure to selectively conduct electricity through one or more areas of substrate 54.

In some examples, substrate 54 may include first major surface 62 adjacent to a respective electrode body (e.g., electrode bodies 18). For example, first major surface may be adhered to a respective electrode body by an adhesive, formed on a respective electrode body, mechanically coupled to a respective electrode body, or the like. In other examples, first major surface 62 may be adjacent or directly adjacent to protective layer 52. For example, first major surface may be adhered to protective layer 52 by an adhesive, formed on protective layer 52, mechanically coupled to protective layer 52, or the like. In some examples, substrate 54 may include second major surface 64. Second major surface 64 may be adjacent to conductive material 58.

Substrate 54 may define a plurality of wells 56. In some examples, plurality of wells 56 may be disposed on second major surface 64 of substrate 54. For example, well 56 may extend a selected depth from second major surface 64 to well base 66. In other examples, plurality of wells 56 may extend substantially through substrate 54. In some examples, each well of the plurality of wells 56 may be formed in substrate 54 by, for example, etching, lithography, drilling, pressing, ablation via a variety of methods, or the like. In some examples, substrate 54 may be formed to include plurality of wells 56 by, for example, additive manufacturing methods, microreplication, or the like.

Regardless of the technique used to form wells 56, each well may define openings 72. Openings 72 may be any suitable size or shape. For example, openings 72 may be circular, square, triangular, another geometry shape, non-geometric shape, irregular shape, or the like. In one example, openings 72 may include circular openings with a radius of may be between about 0.5 millimeters (mm) and about 4 mm; or about 1 mm, about 2 mm, or about 3 mm. In another example, openings 72 may include square openings with a length of between about 0.5 mm and about 10 mm; or about 1 mm, about 2 mm, or about 3 mm. In some examples, opening 72 of one or more wells 56 may be connected by, for example, a channel on or under the second major surface of substrate 54. The channels may allow fluid or powder flow between two or more wells. In this way, openings 70 may be configured to facilitate the release of an electrolyte material.

Wells 56 may be any suitable size and shape. For example, the selected depth of wells 56 may be between about 0.1 millimeters (mm) and about 10 mm; about 2 mm, about 4 mm, or about 6 mm. In some examples, walls 68 of wells 56 may be substantially perpendicular to second major surface 64 of substrate 56. In other examples, walls 68 of wells 56 may not be perpendicular to second major surface 64 of substrate 54. For example, walls 68 may slope long the length of walls 68 from second major surface 64 to the base 66 inward, outward, or a combination of both, relative to an axis extending from opening 70 perpendicular to second major surface 64. In some examples, the size and shape of wells 56 may be selected based on any one or more of a desired volume of electrolyte material to be contained in electrolyte dispersal pad 50, a viscosity of an electrolyte fluid, a desired pattern of electrolyte material release, surface to volume ratio, compatibility with manufacturing processors, cleanliness and sterilization considerations, material release rate, or thermal properties of materials. For example, wells 56, individually or collectively, may be configured to retain a selected volume of electrolyte material. In this way, plurality of wells 56 may be configured to facilitate the release a selected volume of an electrolyte material.

Figure 4:
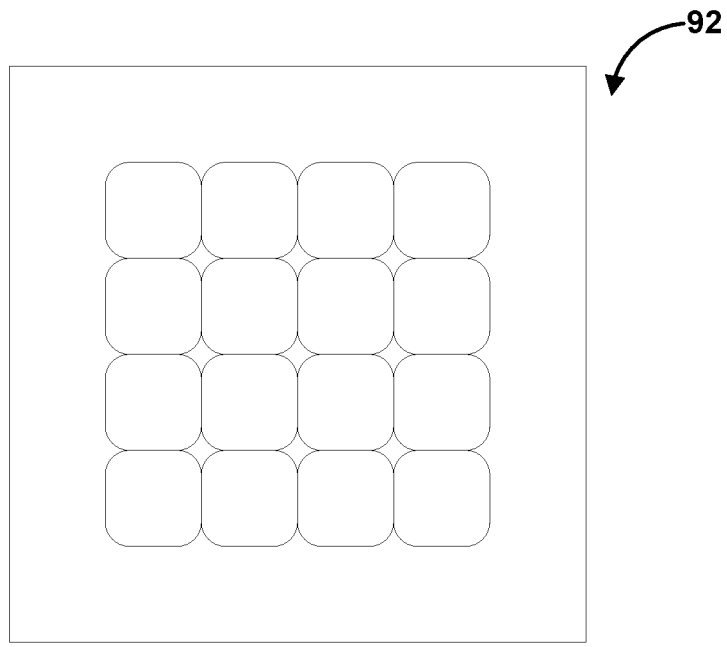
FIGS. 4-7 are conceptual diagrams illustrating example configurations of wells on a conductive electrolyte dispersal pad.
Figure 5:
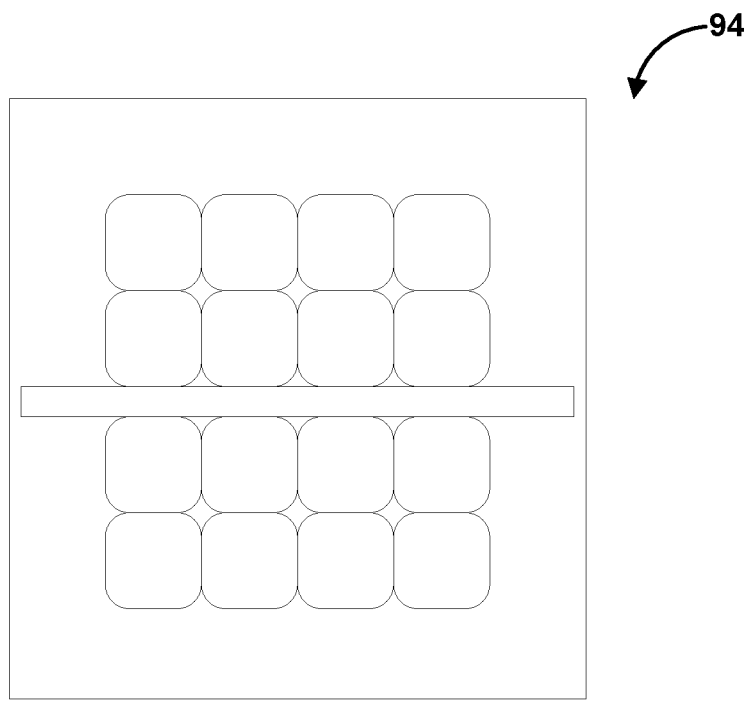
Figure 6:
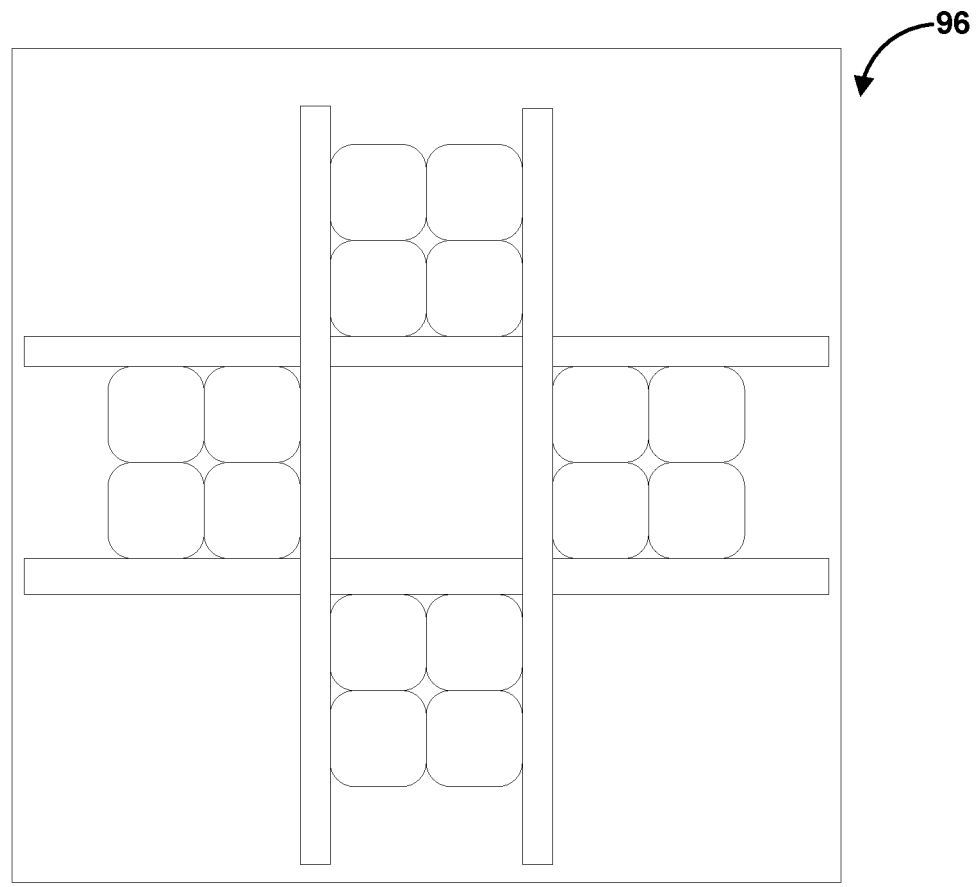
Figure 7:
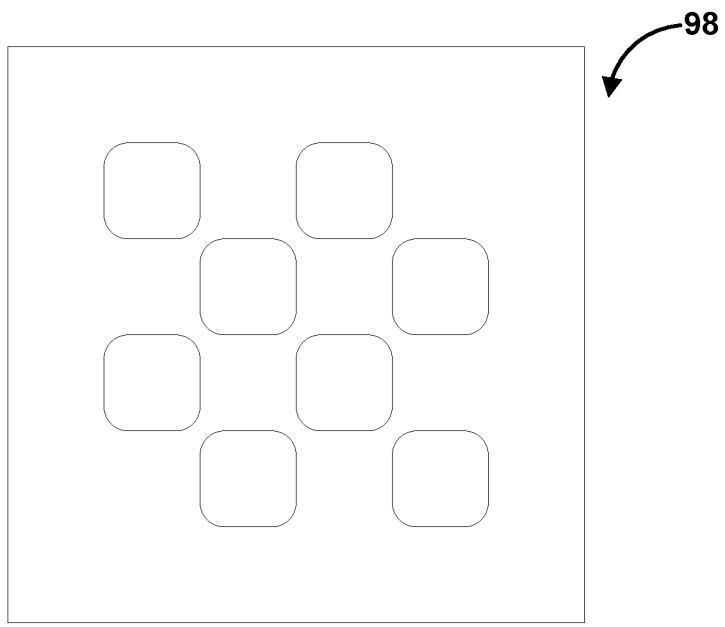

Wells 56 may be formed on, or in, substrate 54 in any suitable configuration. For example, FIGS. 4-7, are conceptual diagrams illustrating example configurations of wells on a conductive electrolyte dispersal pad. In some examples, as shown in FIG. 4, a first configuration 92 of wells 56 may include close packed rows and columns of wells 56. In other examples, as shown in FIG. 5, a second configuration 94 of wells 56 may include a plurality of linear or nonlinear rows (or columns) of wells 56. In other examples, as shown in FIG. 6, a third configuration 96 of wells 56 may include a plurality of groupings of wells 56 in a linear or nonlinear grid pattern. In other examples, as shown in FIG. 7, a fourth configuration 98 of wells 56 may include wells 56 individually spaced apart from other wells in a repeating or nonrepeating pattern. Though FIGS. 4-7 show specific configurations of wells 56 on substrate 54, other configurations are contemplated and are not outside the scope of the present disclosure. For example, wells 56 may be configured in any configuration to retain an electrolyte material in a selected configuration.

In the examples of FIGS. 4-7, each grouping of wells 56, or individual well of a plurality of wells 56, may be separated by second surface 64 of substrate 54. In some examples, a conductive material may be disposed between each grouping of wells 56, or between individual well of a plurality of wells 56. For example, a conductive material (e.g., titanium, copper, silver, gold, aluminum, silicon, or the like) may be disposed on or in second surface 64 of substrate 54 between each grouping of wells 56, or between individual well of a plurality of wells 56. In other examples, a non-conductive material may be disposed between each grouping of wells 56, or individual well of a plurality of wells 56. For example, a nonconductive material (e.g., silicone, rubber, polyethylene, polypropylene, polyurethane, polyvinylchloride, or the like) may be disposed on or in second surface 64 of substrate 54 between each grouping of wells 56, or between individual well of a plurality of wells 56. In this way, second surface 64 of substrate 54 may be configured to pass electric current through a selected path with respect to wells 56.

An electrolyte fluid or powder may be disposed in at least some of wells 56. The electrolyte fluid or powder may be an electrically conductive fluid or powder and/or a low impedance fluid or powder. For example, an electrolyte fluid may include a silver chloride solution, a saline solution, or the like. Electrolyte materials may include any suitable biocompatible fluid or powder with low resistivity properties and useful shelf life duration. The electrolyte material, before release from wells 56, after release from wells 56, or both, may reduce electric resistance at the electrode/skin interface compared to an electrode (e.g., electrode 15) without the electrolyte material. In some examples, before release from wells 56, the electrolyte material may increase the ability of the electrolyte dispersal pad 50 to conform for a contour of the skin of wearer 12. For example, electrolyte material may provide a flexible electrically-conductive pathway through wells 56 to increase the plasticity of electrolyte dispersal pad 50 without an adverse effect on conductivity of electrolyte dispersal pad 50. In other examples, after release from wells 56, an electrolyte material may coat or soak into at least a portion of the skin of the wearer 12, at least a portion of comfort layer 60, or at least a portion of a clothing layer on wearer 12. In this way, the electrolyte material may reduce the impedance at the electrode/skin interface.

As shown in FIG. 3, conductive material 58 may be disposed over at least a portion of the plurality of openings 56. Conductive material 58 may be configured to retain the electrolyte material within the plurality of wells 56. For example, conductive material 58 may be adhered to, or otherwise releasably or permanently attached to, a portion of substrate 54 defining openings 70. In some examples, the size and shape of openings 70 may be configured to improve retention of the electrolyte material within the plurality of wells 56. For example, second major surface 64 may have sufficient surface area in contact with conductive material 58 to allow conductive material 58 to remain adhered to second major surface 64 while WAED system 10 is worn by wearer 12.

In some examples, conductive material 58 may be configured to transmit an electric current. For example, conductive material 58 may include a biocompatible electrically conductive material (e.g., titanium, copper, silver, gold, aluminum, or the like). In some examples, conductive material 58 may be configured to fuse after transmitting a selected electric current for a selected duration. For example, the thickness and resistivity of conductive material 58 may be selected to fuse (e.g., melt or soften) at least a portion 80 of conductive material 58 when a current pulse (e.g., a current of a selected range of amperage, voltage, and/or duration) passes through at least the portion 80 of conductive material 58.

In some examples, conductive material 58 may be electrically coupled to WAED controller 22 via a plurality of electrical conductors of an electrode lead and a plurality of conductive material connections. One example, as shown in FIG. 3, may include conductive material 58 electrically coupled to WAED controller 22 via electrical conductor 76 (e.g., electrical conductors of electrode leads 24) and conductive material connections 78A and 78B (collectively, "conductive material connections 78"). In some examples, electrolyte dispersal pad 50 may include a plurality of conductive material connections disposed in a plurality of locations on conductive material 58. Conductive material connections 78 may include any suitable electrically conductive material. For example, conductive material connections 78 may include conductive metals (e.g., titanium, copper, silver, gold, aluminum, or the like) or other conductive materials (e.g., carbon, silicon, or the like). In some examples, conductive material connections 78 may include detachable connections, e.g., binding post, plug and socket, blade connectors, ring and spade terminals, or other keyed or unkeyed electrical connectors. In other examples, conductive material connections 78 may include permanent or semi-permanent connections, e.g., soldered connections or conductive vias. In some examples, as shown in FIG. 3, conductive material connections 78 may be configured to pass an electric current pulse through at least a portion 80 of conductive material 58. For example, WAED controller may cause a selected electric pulse of a selected duration to pass through the conductive material of portion 80. The electric pulse may fuse (e.g., melt or soften) at least some of the conductive material of portion 80. The fused portion 80 may release electrolyte material from wells 56 adjacent to portion 80. In this way, a WAED controller 22 may cause electric pulses to selectively release an electrolyte material from one or more portions of an electrolyte dispersal pad 50.

In some examples, electrolyte dispersal pad 50 may include a comfort layer 60 disposed between conductive material 58 and the skin of wearer 12. Comfort layer 60 may include any suitable material. For example, comfort layer 60 may include a textile (e.g., cotton, linen, wool, polyester, nylon, of the like). In some examples, comfort layer 60 may include a conductive textile. For example, a conductive textile may include metal strands (e.g., titanium, copper, silver, gold, nickel, or carbon) woven into a textile material or a textile impregnated with a conductive powder (e.g., a carbon or metal powder). In this way, comfort layer may reduce the impedance at the electrode/skin interface. In some examples, comfort layer 60 may be configured to absorb an electrolyte fluid. For example, comfort layer 60 may transport electrolyte fluid from wells 56 to the skin of wearer 12 by a wicking action. In this way, comfort layer 60 may decrease the duration of time necessary for an electrolyte fluid to travel from wells 56 to the skin of wearer 12.

Figure 8:
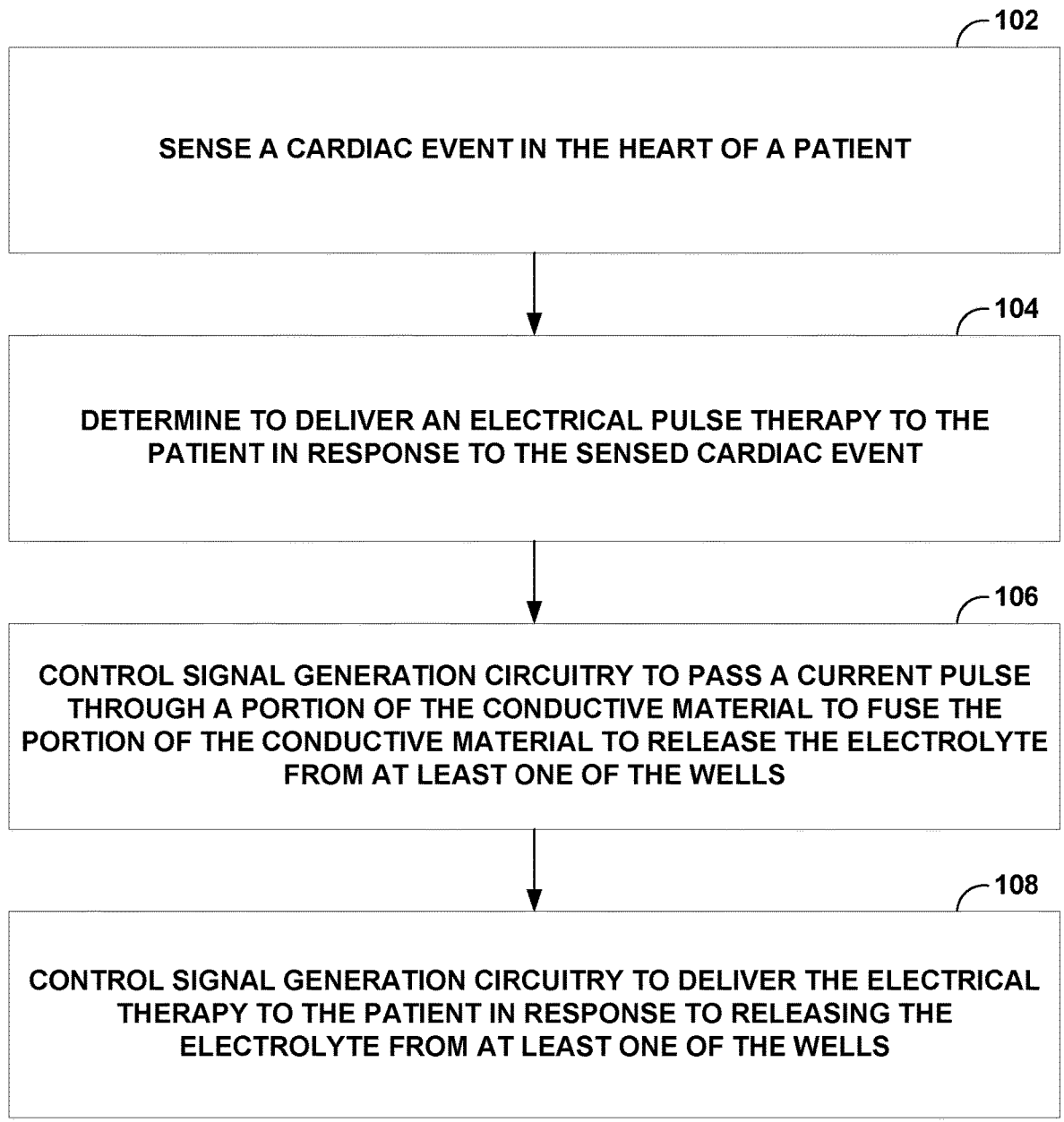
FIG. 8 is a flow diagram illustrating an example method of dispersing a conductive electrolyte material in accordance with one or more examples described in this disclosure.

FIG. 8 is a flow diagram illustrating an example technique of dispersing a conductive electrolyte material in accordance with one or more examples described in this disclosure. The technique of FIG. 8 will be described with respect to WAED system 10 of FIG. 1, WAED controller 22 of FIG. 2, and electrolyte dispersal pad 50 of FIG. 3 for ease of description only. A person having ordinary skill in the art will recognize and appreciate that the technique of FIG. 8 may be used with systems, controllers, and dispersal pads other than other described in FIGS. 1-3.

In some examples, the technique of FIG. 8 may include sensing, by sensing circuitry 32 communicatively coupled to a plurality of electrodes 15 and/or other sensing devices, a cardiac event in the heart of a patient (102). For example, as described above, sensing circuitry 32 configured to receive from electrodes 15 and/or other sensing devices one or more electrical signals indicative of a cardiac event, such as electrical signals produced by heart 13, respiration rate of wearer 12, tissue perfusion of wearer 13, or the like.

In some examples, the technique of FIG. 8 may include determining, by a processing circuitry 30 communicatively coupled to the sensing circuitry 32, in response to the sensed cardiac event, to deliver an electrical pulse therapy to the patient (104). For example, as described above, processing circuitry 30 may process the signals from sensing circuitry 32 to monitor electrical activity of heart 13 of wearer 12. Processing circuitry 30 may store and analyze signals obtained by sensing circuitry 32 or received from memory 40 to determine if signals are indicative of a cardiac event (e.g., tachycardia). In this way, in response to a cardiac event, processing circuitry 30 may determine to deliver an electrical pulse therapy (e.g., a defibrillation shock).

In some examples, the technique of FIG. 8 may include, after determining to deliver an electrical pulse therapy, releasing the electrolyte material from at least one of the wells 56 of an electrolyte distribution pad 50. Releasing the electrolyte material may include controlling, by the processing circuitry 30, the signal generation circuitry 36 and power source 42 to pass a current pulse through a portion 80 of the conductive material 54 to fuse the portion 80 of the conductive material 54 to release the electrolyte material from at least one of the wells 56 (106). For example, as described above, WAED controller 22 may cause electric pulses to selectively release an electrolyte material from one or more portions of an electrolyte dispersal pad 50.

In some examples, the technique of FIG. 8 may include, in response to releasing the electrolyte material from at least one of the wells 56, controlling, by the processing circuitry 30, the signal generation circuitry 36 and power source 42 to deliver the electrical therapy to the wearer 12 (108). For example, as described above, signal generation circuitry 36 may be configured to use energy from power source 42 to deliver an electrical pulse therapy.

In some examples, each respective electrode of a WAED system may include a plurality of electrical connections (e.g., conductive material connections 78) electrically coupled to switching circuitry 34. For example, the plurality of conductive material connections 78 may include a first, second, third, and fourth conductive material connections 78 electrically coupled to conductive material 58 of electrolyte dispersal pad 50 at a respective first, second, third, and fourth position. In such examples, the technique of FIG. 8 may include controlling, by the processing circuitry 30, switching circuitry 34 to pass a first portion of the current pulse from the first position, through a first portion of conductive material 58, to the second position to fuse the first portion of conductive material 58 to release the electrolyte material from at least one first well of the plurality of wells 56, and controlling, by the processing circuitry 30, switching circuitry 34 to pass a second portion of the current pulse from the third position, through a second portion of conductive material 58, to the fourth position to fuse the second portion of conductive material 58 to release the electrolyte material from at least one second well of the plurality of wells 56. In other examples, a WAED system may include a tens or hundreds of electrical connections electrically coupled to switching circuitry 34 such that processing circuitry 30 and/or switching circuitry 34 may selectively fuse portions of conductive material 58. In this way, processing circuitry 30 and/or switching circuitry 34 may selectively fuse portions of conductive material 58 to release an electrolyte material from wells 56 more effectively compared to electrolyte dispersal systems without processing circuitry 30 and/or switching circuitry 34.

The systems and techniques of the disclosure may include, for example, the following numbered statements.

Statement 1: An external defibrillator system, the system comprising: processing circuitry; signal generation circuitry communicatively coupled to the processing circuitry; and a plurality of electrodes, each respective electrode comprising: an electrode body electrically coupled to the signal generation circuitry and configured to deliver an electrical pulse therapy to a patient; and an electrolyte dispersal pad over the electrode body, the electrolyte dispersal pad comprising: a substrate defining a plurality of wells, each respective well defining an opening; an electrolyte material disposed within the plurality of wells; and a conductive material disposed over at least a portion of the plurality of openings and configured to retain the electrolyte material within the plurality of wells, wherein: the processing circuitry is configured control the signal generation circuitry to pass a current pulse through a portion of the conductive material to fuse the portion of the conductive material to release the electrolyte material from at least one of the wells.

Statement 2: The system of statement 1, wherein the processing circuitry is configured to cause the signal generation circuitry to pass the current pulse through the portion of the conductive material to fuse the portion of the conductive material to release the electrolyte material from at least one of the wells prior to controlling the signal generation circuitry to deliver an electrical pulse therapy to the patient.

Statement 3: The system of statement 1 or 2, further comprising switching circuitry electrically coupled to the signal generation circuitry and communicatively coupled to the processing circuitry wherein: each respective electrode further comprises a plurality of electrical connections electrically coupled to the switching circuitry, the plurality of electrical connections comprising: a first electrical connection electrically coupled to the conductive material at a first position; a second electrical connection electrically coupled to the conductive material at a second position; a third electrical connection electrically coupled to the conductive material at a third position; and a fourth electrical connection electrically coupled to the conductive material at a fourth position, wherein: the switching circuitry is configured to pass a first portion of the current pulse from the first position, through a first portion of the conductive material, to the second position to fuse the first portion of the conductive material to release the electrolyte material from at least one first well of the plurality of wells, and the switching circuitry is configured to pass a second portion of the current pulse from the third position, through a second portion of the conductive material, to the fourth position to fuse the second portion of the conductive material to release the electrolyte material from at least one second well of the plurality of wells.

Statement 4: The system of statement 3, wherein: the processing circuitry is configured cause the signal generation circuitry to pass a first current pulse to the switching circuitry and to pass a second, different current pulse to the switching circuitry, the first portion of the current pulse comprises the first current pulse, and the second portion of the current pulse comprises the second, different current pulse.

Statement 5: The system of any one of statements 1 to 4, wherein the conductive material comprises aluminum or titanium.

Statement 6: The system of any one of statements 1 to 5, wherein the substrate comprises silicon.

Statement 7: The system of any one of statements 1 to 6, wherein the electrolyte material is configured to reduce the impedance between a skin of the patient and the electrode body during an electrical pulse therapy.

Statement 8: The system of any one of statements 1 to 7, wherein the electrolyte material is configured to increase the surface area on the skin of the patient through which an electrical pulse passes during an electrical pulse therapy.

Statement 9: The system of any one of statements 1 to 8, wherein the electrolyte material comprises an electrolyte powder.

Statement 10: The system of any one of statements 1 to 8, wherein the electrolyte material comprises an electrolyte fluid.

Statement 11: The system of statement 10, wherein the electrolyte fluid comprises at least one of a saline solution or a silver chloride solution.

Statement 12: The system of any one of statements 1 to 11, wherein the electrolyte dispersal pad is conformal to a contour of a surface of a skin of the patient.

Statement 13: The system of any one of statements 1 to 12, wherein: the system is mounted on a garment wearable by the patient, and the plurality of electrodes are disposed on the garment to pass the electrical pulse therapy through at least a portion of the heart of the patient.

Statement 14: The system of any one of statements 1 to 13, the plurality of electrodes further comprising a textile adjacent the conductive material and a body of the patient, wherein the textile is configured to allow the electrolyte material to pass from the plurality of wells, through the textile, to the body of the patient.

Statement 15: The system of statement 14, wherein the textile comprises an electrically conductive textile.

Statement 16: An external defibrillator electrode electrolyte dispersal pad, the electrolyte dispersal pad comprising: a substrate defining a plurality of wells, each respective well defining an opening; an electrolyte material disposed within the plurality of wells; and a conductive material disposed over at least a portion of the plurality of openings and configured to retain the electrolyte material within the plurality of wells, wherein the conductive material is configured to receive a current pulse through a portion of the conductive material to fuse the portion of the conductive material to release the electrolyte material from at least one of the wells.

Statement 17: The electrolyte dispersal pad of statement 16, further comprising: a first electrical connection electrically coupled to the conductive material at a first position; a second electrical connection electrically coupled to the conductive material at a second position; a third electrical connection electrically coupled to the conductive material at a third position; and a fourth electrical connection electrically coupled to the conductive material at a fourth position, wherein: the first electrical connection and second electrical connect are configured to pass a first current pulse from the first position, through a first portion of the conductive material, to the second position to fuse the first portion of the conductive material to release the electrolyte material from at least one first well of the plurality of wells, and the third electrical connection and fourth electrical connection are configured to pass a second portion of the current pulse from the third position, through a second portion of the conductive material, to the fourth position to fuse the second portion of the conductive material to release the electrolyte material from at least one second well of the plurality of wells.

Statement 18: The electrolyte dispersal pad of statement 16 or 17, wherein the conductive material comprises aluminum or titanium.

Statement 19: The electrolyte dispersal pad of any one of statements 16 to 18, wherein the substrate comprises silicon.

Statement 20: The electrolyte dispersal pad of any one of statements 16 to 19, wherein the electrolyte material comprises an electrolyte powder.

Statement 21: The electrolyte dispersal pad of any one of statements 16 to 19, wherein the electrolyte material comprises an electrolyte fluid.

Statement 22: The electrolyte dispersal pad of statement 21, wherein the electrolyte fluid comprises at least one of a saline solution or a silver chloride solution.

Statement 23: The electrolyte dispersal pad of any one of statements 16 to 22, wherein the electrolyte dispersal pad is conformal to a contour of a surface of a skin of the patient.

Statement 24: The electrolyte dispersal pad of any one of statements 16 to 23, wherein the electrolyte dispersal pad configured to be receivable on a garment wearable by a patient.

Statement 25: The electrolyte dispersal pad of any one of statements 16 to 24, the electrolyte dispersal pad further comprising a textile adjacent the conductive material, wherein the textile is configured to allow the electrolyte material to pass from the plurality of wells through the textile.

Statement 26: The electrolyte dispersal pad of statement 25, wherein the textile comprises an electrically conductive textile.

Statement 27: A method comprising: sensing, by sensing circuitry communicatively coupled to a plurality of electrodes, a cardiac event in a heart of a patient, wherein each respective electrode comprises: an electrode body electrically coupled to a signal generation circuitry and configured to deliver an electrical pulse therapy to the patient; and an electrolyte dispersal pad over the electrode body, the electrolyte dispersal pad comprising: a substrate defining a plurality of wells, each respective well defining an opening; an electrolyte material disposed within the plurality of wells; and a conductive material disposed over at least a portion of the plurality of openings and configured to retain the electrolyte material within the plurality of wells; determining, by processing circuitry communicatively coupled to the sensing circuitry, in response to the sensed cardiac event, to deliver an electrical pulse therapy to the patient; and releasing the electrolyte material from at least one of the wells by at least: controlling, by the processing circuitry, the signal generation circuitry to pass a current pulse through a portion of the conductive material to fuse the portion of the conductive material to release the electrolyte material from at least one of the wells.

Statement 28: The method of statement 27, further comprising controlling, by the processing circuitry, in response to releasing the electrolyte material from at least one of the wells, the signal generation circuitry to deliver the electrical therapy to the patient.

Statement 29: The method of statement 27 or 28, wherein: each respective electrode further comprises a plurality of electrical connections electrically coupled to a switching circuitry, the plurality of electrical connections comprising: a first electrical connection electrically coupled to the conductive material at a first position; a second electrical connection electrically coupled to the conductive material at a second position; a third electrical connection electrically coupled to the conductive material at a third position; and a fourth electrical connection electrically coupled to the conductive material at a fourth position, controlling, by the processing circuitry, the switching circuitry to pass the current pulse through a portion of the conductive material to fuse the portion of the conductive material to release the electrolyte material from at least one of the wells, further comprises: controlling, by the processing circuitry, the switching circuitry to pass a first portion of the current pulse from the first position, through a first portion of the conductive material, to the second position to fuse the first portion of the conductive material to release the electrolyte material from at least one first well of the plurality of wells, and controlling, by the processing circuitry, the switching circuitry to pass a second portion of the current pulse from the third position, through a second portion of the conductive material, to the fourth position to fuse the second portion of the conductive material to release the electrolyte material from at least one second well of the plurality of wells.

Statement 30: The method of statement 29, wherein: the first portion of the current pulse comprises a first current pulse, the second portion of the current pulse comprises a second, different current pulse, and controlling, by the processing circuitry, the signal generation circuitry to pass a current pulse to a switching circuitry comprises controlling, by the processing circuitry, the signal generation circuitry to pass the first current pulse to the switching circuitry, and, after the first current pulse, controlling, by the processing circuitry, the signal generation circuitry to pass the second current pulse to the switching circuitry.

Statement 31: The method of any one of statements 27 to 30, wherein the conductive material comprises aluminum or titanium.

Statement 32: The method of any one of statements 27 to 31, wherein the substrate comprises silicon.

Statement 33: The method of any one of statements 27 to 32, wherein the electrolyte material is configured to reduce the impedance between a skin of the patient and the electrode body during an electrical pulse therapy.

Statement 34: The method of any one of statements 27 to 33, wherein the electrolyte material is configured to increase the surface area on the skin of the patient through which an electrical pulse passes during an electrical pulse therapy.

Statement 35: The system of any one of statements 27 to 34, wherein the electrolyte material comprises an electrolyte powder.

Statement 36: The system of any one of statements 27 to 34, wherein the electrolyte material comprises an electrolyte fluid.

Statement 37: The method of statement 36, wherein the electrolyte fluid comprises at least one of a saline solution or a silver chloride solution.

Statement 38: The method of any one of statements 27 to 37, wherein the electrolyte dispersal pad is conformal to a contour of a surface of a skin of the patient.

Statement 39: The method of any one of statements 27 to 38, wherein: the system is mounted on a garment wearable by the patient, and the plurality of electrodes are disposed on the garment to pass the electrical pulse therapy through at least a portion of the heart of the patient.

Statement 40: The method of any one of statements 27 to 39, the plurality of electrodes further comprising a textile adjacent the conductive material and a body of the patient, wherein the textile is configured to allow the electrolyte material to pass from the plurality of wells, through the textile, to the body of the patient.

Statement 41: The method of statement 40, wherein the textile comprises an electrically conductive textile.

Statement 42: The method of any one of statements 27 to 35, further comprising communicating, by user interface, the determination to deliver the electrical pulse therapy.

Statement 43: The method of any one of statements 27 to 42, further comprising storing, by a memory, any one of the sensing of the cardiac event, the determination to deliver the electrical pulse therapy, or controlling the signal generating circuitry to deliver the electrical pulse therapy.

Statement 44: A wearable external defibrillator system, the system comprising: processing circuitry; signal generation circuitry communicatively coupled to the processing circuitry; and a plurality of electrodes, each respective electrode comprising: an electrode body electrically coupled to the signal generation circuitry and configured to deliver an electrical pulse therapy to a patient; and an electrolyte dispersal pad over the electrode body wherein the electrolyte dispersal pad is conformal to a contour of a surface of a skin of the patient, the electrolyte dispersal pad comprising: a substrate defining a plurality of wells, each respective well defining an opening; an electrolyte material disposed within the plurality of wells, wherein the electrolyte material is configured to reduce the impedance between the skin of the patient and the electrode body during an electrical pulse therapy and increase the surface area on the skin of the patient through which an electrical pulse passes during an electrical pulse therapy; and a conductive material disposed over at least a portion of the plurality of openings and configured to retain the electrolyte material within the plurality of wells, wherein: the processing circuitry is configured control the signal generation circuitry to pass a current pulse through a portion of the conductive material to fuse the portion of the conductive material to release the electrolyte material from at least one of the wells prior to controlling the signal generation circuitry to deliver an electrical pulse therapy to the patient.

Various examples have been described. These and other examples are within the scope of the claims.

The invention claimed is:

1. An external defibrillator system, the system comprising:
processing circuitry;
signal generation circuitry communicatively coupled to the processing circuitry; and
a plurality of electrodes, each respective electrode comprising:
an electrode body electrically coupled to the signal generation circuitry and configured to deliver an electrical pulse therapy to a patient; and
an electrolyte dispersal pad over the electrode body, the electrolyte dispersal pad comprising:
a substrate having a first surface adjacent the electrode body and a second surface opposing the first surface, wherein the second surface defines a plurality of wells, each respective well defining an opening;
an electrolyte material disposed within the plurality of wells; and
a conductive material disposed adjacent the second surface over at least a portion of the plurality of openings and configured to retain the electrolyte material within the plurality of wells,
wherein the processing circuitry is configured control the signal generation circuitry to pass a current pulse through a portion of the conductive material, and
wherein the portion of the conductive material is configured to, in response to the current pulse, fuse to release the electrolyte material from at least one of the wells.

2. The system of claim 1, wherein the processing circuitry is configured to cause the signal generation circuitry to pass the current pulse through the portion of the conductive material to fuse the portion of the conductive material to release the electrolyte material from at least one of the wells prior to controlling the signal generation circuitry to deliver an electrical pulse therapy to the patient.

3. The system of claim 1, further comprising switching circuitry electrically coupled to the signal generation circuitry and communicatively coupled to the processing circuitry wherein:
each respective electrode further comprises a plurality of electrical connections electrically coupled to the switching circuitry, the plurality of electrical connections comprising:
a first electrical connection electrically coupled to the conductive material at a first position;
a second electrical connection electrically coupled to the conductive material at a second position;
a third electrical connection electrically coupled to the conductive material at a third position; and
a fourth electrical connection electrically coupled to the conductive material at a fourth position,
wherein:
the switching circuitry is configured to pass a first portion of the current pulse from the first position, through a first portion of the conductive material, to the second position to fuse the first portion of the conductive material to release the electrolyte material from at least one first well of the plurality of wells, and
the switching circuitry is configured to pass a second portion of the current pulse from the third position, through a second portion of the conductive material, to the fourth position to fuse the second portion of the conductive material to release the electrolyte material from at least one second well of the plurality of wells.

4. The system of claim 3, wherein:
the processing circuitry is configured cause the signal generation circuitry to pass a first current pulse to the switching circuitry and to pass a second, different current pulse to the switching circuitry,
the first portion of the current pulse comprises the first current pulse, and
the second portion of the current pulse comprises the second, different current pulse.

5. The system of claim 1, wherein the conductive material comprises aluminum or titanium.

6. The system of claim 1, wherein the substrate comprises silicon.

7. The system of claim 1, wherein the electrolyte material is configured to reduce the impedance between a skin of the patient and the electrode body during an electrical pulse therapy.

8. The system of claim 1, wherein the electrolyte material is configured to increase the surface area on the skin of the patient through which an electrical pulse passes during an electrical pulse therapy.

9. The system of claim 1, wherein the electrolyte material comprises an electrolyte powder.

10. The system of claim 1, wherein the electrolyte material comprises an electrolyte fluid.

11. The system of claim 10, wherein the electrolyte fluid comprises at least one of a saline solution or a silver chloride solution.

12. The system of claim 1, wherein the electrolyte dispersal pad is conformal to a contour of a surface of a skin of the patient.

13. The system of claim 1, wherein:
the system is mounted on a garment wearable by the patient, and
the plurality of electrodes are disposed on the garment to pass the electrical pulse therapy through at least a portion of the heart of the patient.

14. The system of claim 1, the plurality of electrodes further comprising a textile adjacent the conductive material and a body of the patient, wherein the textile is configured to allow the electrolyte material to pass from the plurality of wells, through the textile, to the body of the patient.

15. The system of claim 14, wherein the textile comprises an electrically conductive textile.

16. An external defibrillator electrode electrolyte dispersal pad, the electrolyte dispersal pad comprising:
a substrate having a first surface adjacent the electrode body and a second surface opposing the first surface, wherein the second surface defines a plurality of wells, each respective well defining an opening;
an electrolyte material disposed within the plurality of wells; and
a conductive material disposed adjacent the second surface over at least a portion of the plurality of openings and configured to retain the electrolyte material within the plurality of wells, wherein the conductive material is configured to receive a current pulse through a portion of the conductive material, and wherein the portion of the conductive material is configured to, in response to the current pulse, fuse to release the electrolyte material from at least one of the wells.

17. The electrolyte dispersal pad of claim 16, further comprising:
a first electrical connection electrically coupled to the conductive material at a first position;
a second electrical connection electrically coupled to the conductive material at a second position;
a third electrical connection electrically coupled to the conductive material at a third position; and
a fourth electrical connection electrically coupled to the conductive material at a fourth position, wherein:
the first electrical connection and second electrical connect are configured to pass a first current pulse from the first position, through a first portion of the conductive material, to the second position to fuse the first portion of the conductive material to release the electrolyte material from at least one first well of the plurality of wells, and
the third electrical connection and fourth electrical connection are configured to pass a second portion of the current pulse from the third position, through a second portion of the conductive material, to the fourth position to fuse the second portion of the conductive material to release the electrolyte material from at least one second well of the plurality of wells.

18. The electrolyte dispersal pad of claim 16, wherein the conductive material comprises aluminum or titanium.

19. The electrolyte dispersal pad of claim 16, wherein the substrate comprises silicon.

20. The electrolyte dispersal pad of claim 16, wherein the electrolyte material comprises an electrolyte powder.

21. The electrolyte dispersal pad of claim 16, wherein the electrolyte material comprises an electrolyte fluid.

22. The electrolyte dispersal pad of claim 21, wherein the electrolyte fluid comprises at least one of a saline solution or a silver chloride solution.

23. The electrolyte dispersal pad of claim 16, wherein the electrolyte dispersal pad is conformal to a contour of a surface of a skin of the patient.

24. The electrolyte dispersal pad of claim 16, wherein the electrolyte dispersal pad configured to be receivable on a garment wearable by a patient.

25. The electrolyte dispersal pad of claim 16, the electrolyte dispersal pad further comprising a textile adjacent the conductive material, wherein the textile is configured to allow the electrolyte material to pass from the plurality of wells through the textile.

26. The electrolyte dispersal pad of claim 25, wherein the textile comprises an electrically conductive textile.

27. A method comprising:
sensing, by sensing circuitry communicatively coupled to a plurality of electrodes, a cardiac event in a heart of a patient, wherein each respective electrode comprises:
an electrode body electrically coupled to a signal generation circuitry and configured to deliver an electrical pulse therapy to the patient; and
an electrolyte dispersal pad over the electrode body, the electrolyte dispersal pad comprising:
a substrate having a first surface adjacent the electrode body and a second surface opposing the first surface, wherein the second surface defines a plurality of wells, each respective well defining an opening;
an electrolyte material disposed within the plurality of wells; and
a conductive material disposed adjacent the second surface over at least a portion of the plurality of openings and configured to retain the electrolyte material within the plurality of wells;

determining, by processing circuitry communicatively coupled to the sensing circuitry, in response to the sensed cardiac event, to deliver an electrical pulse therapy to the patient; and releasing the electrolyte material from at least one of the wells by at least:

controlling, by the processing circuitry, the signal generation circuitry to pass a current pulse through a portion of the conductive material, wherein the portion of the conductive material is configured to, in response to the current pulse, fuse to release the electrolyte material from at least one of the wells.

28. The method of claim 27, further comprising controlling, by the processing circuitry, in response to releasing the electrolyte material from at least one of the wells, the signal generation circuitry to deliver the electrical therapy to the patient.

29. The method of claim 27, wherein:

each respective electrode further comprises a plurality of electrical connections electrically coupled to a switching circuitry, the plurality of electrical connections comprising:

a first electrical connection electrically coupled to the conductive material at a first position;

a second electrical connection electrically coupled to the conductive material at a second position;

a third electrical connection electrically coupled to the conductive material at a third position; and a fourth electrical connection electrically coupled to the conductive material at a fourth position, controlling, by the processing circuitry, the switching circuitry to pass the current pulse through a portion of the conductive material to fuse the portion of the conductive material to release the electrolyte material from at least one of the wells, further comprises:

controlling, by the processing circuitry, the switching circuitry to pass a first portion of the current pulse from the first position, through a first portion of the conductive material, to the second position to fuse the first portion of the conductive material to release the electrolyte material from at least one first well of the plurality of wells, and controlling, by the processing circuitry, the switching circuitry to pass a second portion of the current pulse from the third position, through a second portion of the conductive material, to the fourth position to fuse the second portion of the conductive material to release the electrolyte material from at least one second well of the plurality of wells.

30. The method of claim 29, wherein:

the first portion of the current pulse comprises a first current pulse, the second portion of the current pulse comprises a second, different current pulse, and controlling, by the processing circuitry, the signal generation circuitry to pass a current pulse to a switching circuitry comprises controlling, by the processing circuitry, the signal generation circuitry to pass the first current pulse to the switching circuitry, and, after the first current pulse, controlling, by the processing circuitry, the signal generation circuitry to pass the second current pulse to the switching circuitry.

31. The method of claim 27, wherein the conductive material comprises aluminum or titanium.

32. The method of claim 27, wherein the substrate comprises silicon.

33. The method of claim 27, wherein the electrolyte material is configured to reduce the impedance between a skin of the patient and the electrode body during an electrical pulse therapy.

34. The method of claim 27, wherein the electrolyte material is configured to increase the surface area on the skin of the patient through which an electrical pulse passes during an electrical pulse therapy.

35. The system of claim 27, wherein the electrolyte material comprises an electrolyte powder.

36. The system of claim 27, wherein the electrolyte material comprises an electrolyte fluid.

37. The method of claim 36, wherein the electrolyte fluid comprises at least one of a saline solution or a silver chloride solution.

38. The method of claim 27, wherein the electrolyte dispersal pad is conformal to a contour of a surface of a skin of the patient.

39. The method of claim 27, wherein:

the system is mounted on a garment wearable by the patient, and the plurality of electrodes are disposed on the garment to pass the electrical pulse therapy through at least a portion of the heart of the patient.

40. The method of claim 27, the plurality of electrodes further comprising a textile adjacent the conductive material and a body of the patient, wherein the textile is configured to allow the electrolyte material to pass from the plurality of wells, through the textile, to the body of the patient.

41. The method of claim 40, wherein the textile comprises an electrically conductive textile.

42. The method of claim 27, further comprising communicating, by user interface, the determination to deliver the electrical pulse therapy.

43. The method of claim 27, further comprising storing, by a memory, any one of the sensing of the cardiac event, the determination to deliver the electrical pulse therapy, or controlling the signal generating circuitry to deliver the electrical pulse therapy.

44. A wearable external defibrillator system, the system comprising:

processing circuitry;

signal generation circuitry communicatively coupled to the processing circuitry; and a plurality of electrodes, each respective electrode comprising:

an electrode body electrically coupled to the signal generation circuitry and configured to deliver an electrical pulse therapy to a patient; and an electrolyte dispersal pad over the electrode body wherein the electrolyte dispersal pad is conformal to a contour of a surface of a skin of the patient, the electrolyte dispersal pad comprising:

a substrate having a first surface adjacent the electrode body and a second surface opposing the first surface, wherein the second surface defines a plurality of wells, each respective well defining an opening;

an electrolyte material disposed within the plurality of wells, wherein the electrolyte material is configured to reduce the impedance between the skin of the patient and the electrode body during an electrical pulse therapy and increase the surface area on the skin of the patient through which an electrical pulse passes during an electrical pulse therapy; and a conductive material adjacent the second surface disposed over at least a portion of the plurality of openings and configured to retain the electrolyte material within the plurality of wells, wherein the processing circuitry is configured control the signal generation circuitry to pass a current pulse through a portion of the conductive material, and wherein the portion of the conductive material is configured to, in response to the current pulse, fuse to release the electrolyte material from at least one of the wells.

* * * * *